73-626
9/23/80    OR    4,223,560

United States Patent [19]
Glenn

[11] 4,223,560
[45] Sep. 23, 1980

[54] VARIABLE DELAY SYSTEM

[75] Inventor: William E. Glenn, Fort Lauderdale, Fla.

[73] Assignee: New York Institute of Technology, Old Westbury, N.Y.

[21] Appl. No.: 430

[22] Filed: Jan. 2, 1979

[51] Int. Cl.³ .................... G01N 29/00; H03H 19/00
[52] U.S. Cl. ........................................ 73/626; 333/165
[58] Field of Search ............... 73/609, 620, 625, 626, 73/628; 128/660; 340/1 R, 3 R; 333/165; 367/103, 105, 119, 138

[56] References Cited
U.S. PATENT DOCUMENTS

| | | | |
|---|---|---|---|
| 2,406,340 | 8/1946 | Batchelder | 367/123 |
| 4,005,382 | 1/1977 | Beaver | 73/626 |
| 4,012,952 | 3/1977 | Dory | 73/626 |
| 4,019,169 | 4/1977 | Takamizawa | 73/626 |
| 4,116,229 | 9/1978 | Pering | 73/626 |
| 4,127,034 | 11/1978 | Lederman et al. | 73/626 |

Primary Examiner—Stephen A. Kreitman
Attorney, Agent, or Firm—Martin Novack

[57] ABSTRACT

A variable delay system in which multistage delay lines are "shared" between different elements (e.g. different transducer elements or segments). A plurality of delay lines are provided, the delay lines having respectively different numbers of stages. The signals from the first and last segments of a segmented transducer are applied to opposing ends of the delay line having the largest number of stages. The signals from the second and next-to-last segments of the transducer are applied to opposing ends of the delay line having the next-to-largest number of stages, and so on. A plurality of coupling circuits are respectively associated with the plurality of delay lines and are operative to sample, as a function of time, the signals at different delay stages of their respective delay lines. The outputs of the coupling circuits are combined to form an image-representative signal.

58 Claims, 4 Drawing Figures

VARIABLE DELAY SYSTEM

BACKGROUND OF THE INVENTION

This invention relates to variable delay techniques and, more particularly, to delay techniques useful for such functions as dynamic focusing or beam steering. The subject matter of this invention is related to subject matter disclosed in my copending U.S. Application Ser. No. 000,429 entitled "Selectable Delay System" filed of even date herewith and assigned to the same assignee as the present application. The invention is especially useful in ultrasonic imaging systems.

In recent years ultrasonic techniques have become more prevalent in clinical diagnosis. Such techniques have been utilized for some time in the field of obstetrics, neurology and cardiology, and are becoming increasingly important in the visualization of subcutaneous blood vessels including imaging of smaller blood vessels.

Various fundamental factors have given rise to the increased use of ultrasonic techniques. Ultrasonic differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signals representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scanlines on the display, and successive transverse positions are utilized to obtain successive scanlines on the display. The technique yields a cross-sectional picture in the plane of the scan, and the resultant display can be viewed directly or recorded photographically or on magnetic tape. The transverse scan of the beam may be achieved by a reflector which is scanned mechanically over a desired angle.

In systems of the type described, the transducer is of finite size, and the beam transmitted and/or received by the transducer has a finite cross seciton which is a limiting factor on the resolution capabilities of the imaging system. It is known that the ultrasound beam can be "focused", by providing a suitable lens, such as is described in the U.S. Pat. No. 3,958,559, and/or by segmenting the transducer and coupling the different transducer segments to the transmitter/receiver circuitry via different delays. One can readily visualize the focusing effect of the segmented transducer in conjunction with different delays by observing that (for a flat transducer without a lens) the ultrasound path to or from a given focal point to each of a plurality of concentric transducer segments is different for each segment. Typically, the geometrical path between the center transducer segment and the focal point is shortest and the geometrical path between the focal point and the outer transducer segment is longest, with the path to each intermediate transducer segment depending upon its size and relative position in the order of segments. Accordingly, ultrasound energy transmitted from the center segment would generally arrive at the focal point before the beam energy transmitted from the outer transducer segments and, similarly, an ultrasound echo reflected from the focal point will return sooner to the center transducer segment than to the outer transducer segments. A given focus can thus be achieved by providing appropriately longer delays (for example, but not necessarily, electronic delays) in conjunction with the central segments of the transducer than are provided for the outer segments thereof.

It is also presently known in the art that the required delays vary as the focal point under consideration varies, as would typically be the case in a pulse echo system wherein information is to be received over a range of depths in the body being investigated by the ultrasound beam. In such instance, it is recognized that using fixed delays the beam is only "focused" at one particular focal length (or depth range), and the different geometries associated with other depths in the body require other delays to achieve an optimum focus at each point. Briefly, this can be visualized by recognizing that as the focal point moves deeper into the body, the difference between arrival times at the various transducer segments becomes less and less. Accordingly, a "dynamic focus" can be achieved (during receiving) by dynamically varying the delays associated with the different transducer segments such that the relative delays added to the more central transducer segments decrease as the focal point moves deeper into the body. Unfortunately, the need to provide a relatively large number of variable delays and circuitry to control these delays renders dynamic focusing an impractical expedient in many applications. The circuitry required therefor typically suffers one or more of the disadvantages of undue size, expense, complexity, and unreliability.

It is one object of the present invention to provide an imaging system and method including a dynamic focusing technique which overcomes disadvantages present in the prior art. It is a further object hereof to provide a variable delay apparatus and method which can be used for beam steering and/or variable focusing applications, among others.

SUMMARY OF THE INVENTION

The present invention is directed to a variable delay system which employs less active elements than comparable existing systems and can achieve such functions as dynamic focusing or beam steering in an efficient manner and with an economy of components. As will become understood, the multistage delay lines employed in the present invention are "shared" between different elements (e.g. different transducer elements or segments). This and other features of the invented system render it advantageous over existing systems.

In general, the present invention is directed to a variable delay system for coupling a plurality of elements to a single element. Typically, the plurality of elements will be ordered elements or segments of a transducer, and a single element will be a variably focused output. However, the single element may alternatively be a source of signal which is coupled, with variable delay, to the plurality of elements, such as in an electrical beam steering technique. A plurality of delay lines are provided, and means are provided for respectively connecting, via suitable amplification or other means, pairs of the elements to opposite ends of different ones of the plurality of delay lines. For example, if the plurality of elements comprises n elements, the pair of elements numbered 1 and n can be connected to opposite ends of one of the delay lines, the elements numbered 2 and n−1 can be connected to the opposite ends of another of the delay lines, and so on. A plurality of coupling means, respectively associated with the plurality of delay lines, are provided, each of the coupling means being operative to couple a selected delay stage of its associated delay line to the single element. Means are then provided for changing the selected delay stages to which the coupling means are coupled.

In the preferred embodiment of the invention the delay lines have different numbers of stages and the coupling means are coupled to the single element via delay means which are operative to introduce successively greater delays between the single element and the delay lines having successively lesser numbers of stages. In this embodiment, the means for changing the selected delay stages to which the coupling means are coupled are operative to sequence, in synchronism with each other, through successive delay stages of each delay line.

The present invention is particularly, although not necessarily, applicable to an apparatus for imaging a body by transmitting ultrasound energy into the body. A transducer is provided for converting ultrasound energy reflected from the body into electrical signals, the transducer being divided into a number of ordered segments. A plurality of delay lines are provided, the delay lines having respectively different numbers of stages. Means are provided for respectively applying the signals from the first and last segments to opposing ends of the delay line having the largest number of stages, for applying the signals from the second and next-to-last segments to opposing ends of the delay line having the next-to-largest number of stages, and so on. A plurality of coupling means are respectively associated with the plurality of delay lines and are operative to sample, as a function of time, the signals at different delay stages of their respective delay lines. Means are then provided for combining the outputs of the coupling means to form an image-representative signal. In the preferred embodiment of this form of the invention, means are provided for generating a plurality of synchronized control signals and for applying the control signals to respective coupling means to control the sampling positions of the coupling means, whereby signals at successive stages of the delay lines are sequentially sampled by the coupling means. Also, in this embodiment the combining means includes delay means which are operative to introduce successively greater fixed delays to the signals from delay lines having successively lesser numbers of stages. As will be described further hereinbelow, this technique effectively "compensates" for the delay lines having different numbers of stages.

In a further form of the invention, a variable delay system is switchable to different (temporarily) fixed delay states under operator control. This configuration is similar to those already described, but the plurality of coupling means need not, in this configuration, be automatically sequenced to sample successive stages of their associated delay lines. Instead, each of the coupling means is operative, under operator control, to couple the signal at an operator selected one of the delay stages to the combining means.

Further features and advantages of the invention will become more readily apparent from the following detailed description when taken in conjunction with the accompanying drawings.

DESCRIPTION OF THE PREFERRED EMBODIMENT

Figure 1:
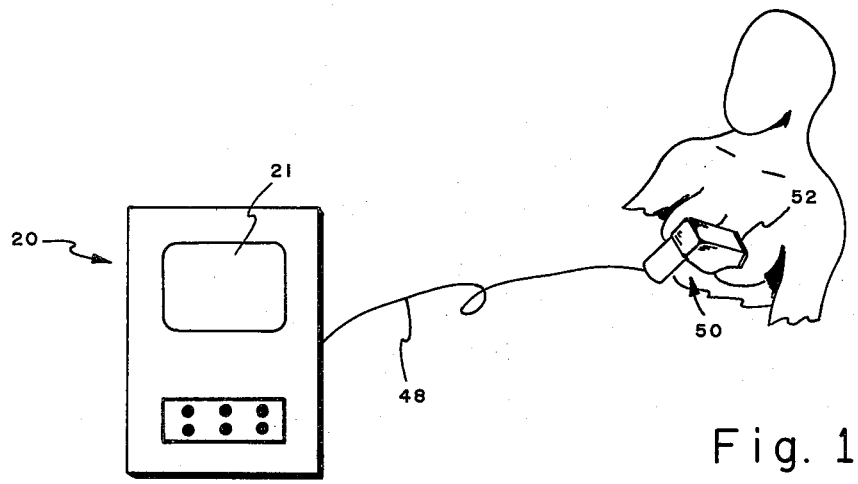
FIG. 1 illustrates the operation of an imaging apparatus which employs the improvements of the invention.

Referring to FIG. 1, there is shown as illustration of a scanning apparatus which employs the improvements of the invention. A console 20 is provided with a display 21 which may typically be a cathode ray tube television-type display, and a suitable control panel. A video tape recorder or suitable photographic means may also be included in the console to effect ultimate display of images. The console will typically house power supplies and portions of the timing and processing circuitry of the system to be described. A portable scanning module or probe 50 is coupled to the console by a cable 48. In the present embodiment the probe has a generally cylindrical handle and a scanning window 52 near one end. During operation of the apparatus, the probe 50 is handheld to position the scanning window over a part of the body to be imaged. For example, in FIG. 1 the probe is positioned such that a cross section of the breast will be obtained. Imaging of other portions of the body is readily attained by moving the probe to the desired position and orientation, the relative orientation of the scanning window determining the angle of the cross section taken.

Figure 2:
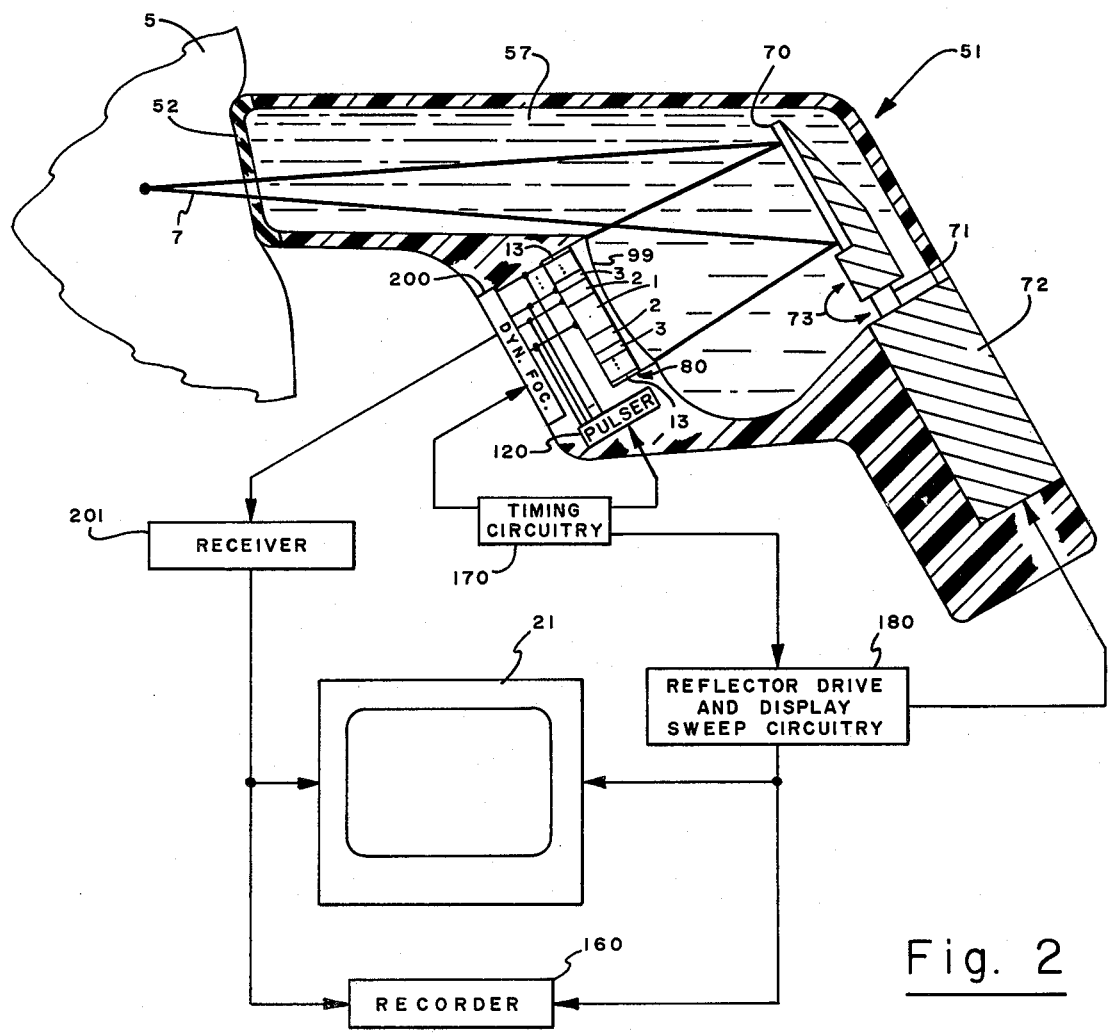
FIG. 2 is a schematic diagram, partially in block form, of an apparatus which employs the improvements of the invention.

Referring to FIG. 2, there is shown a cross-sectional view of a portion of the scanning module or probe 50 along with diagrams of portions of the circuitry therein and in console 20 used in conjunction therewith. An enclosure 51, which may be formed of a study plastic, has scanning window 52 at the front end thereof. The enclosure 51 is filled with a suitable fluid 57, for example, water. The scanning window 52 is relatively flat and may be formed, for example, of polystyrene or nylon. A reflective scanner 70, which is flat in the illustration but which may be curved to provide focusing if desired, is positioned at the approximate rear of the enclosure 51 and substantially faces the window 52. The scanner 70 is mounted on a shaft 71 which passes through a suitable seal and is connected to an electric motor 72 which is mounted in a recess in enclosure 51 and is driven to provide the desired oscillatory motion of scanner 70, as depicted by curved two-headed arrow 73.

An ultrasonic transducer 80, which may have an associated focusing lens 99, is mounted in a compartment 59 of enclosure 51. The transducer is mounted relatively frontwardly of reflective scanner 70 in the module 50 with the ultrasound-emitting face of the transducer generally facing rearwardly in the module 50 and being directed toward the reflective scanner 70. As described in my copending U.S. Application Ser. No. 890,378, assigned to the same assignee as the present application, the transducer 80 is positioned such that the ultrasound beam which it emits is reflected by the scanner 70 to double back past transducer 80 before passing through the window 52. The scanner preferably has a reflective surface formed of a material which results in a relatively small critical angle so that the beam impinging almost directly on the reflector surface will not pass through the reflector. The described arrangement makes efficient use of the volume of fluid 57 in the module 50 since the beam 7 is effectively "doubling back" past the transducer and experiencing a relatively large travel distance through a relatively small volume of water.

The transducer 80 is divided into a plurality of segments, typically a central circular segment surrounded by concentric annular segments. However, as described in my copending U.S. Application Ser. No. 890,377, assigned to the same assignee as the present application, the transducer may alternatively have a generally elliptical shape. Also, for other applications of the invention, for example, beam steering, other transducer configurations, including linear arrays, can be employed. In FIG. 2 only some of thirteen segments designated 1, 2 . . . 13 are shown for ease of illustration, although it will be understood that the principles of the invention are readily applicable regardless of the number of segments employed. The transducer segments 1–13 are coupled to pulser circuitry 120 which provides energizing pulses to the transducer 80 in known manner. The transducer segments are also coupled, via lines 1A, 2A . . . 13A, to novel dynamic focusing circuitry 200 in accordance with the invention. The circuitry 200 is preferably operable, in the illustrated configuration, during the receiving mode and it processes the received echoes in a manner to be described. Suitable preamplification and amplification (not shown in FIG. 2) can be provided in the dynamic focusing circuitry 200 and in receiver 201 which may also include conventional processing electronics, not the subject of this invention. The output of dynamic focusing circuitry 200 is coupled, via receiver 201, to display 21 and recorder 160, which may be any suitable recording or memory means such as a video tape recorder. If desired, gain control circuitry may be provided and may include interactive gain compensation, which is described in detail in U.S. Pat. No. 4,043,181. Interactive gain compensation circuitry compensates the amplitude of later arriving signals for attenuation experienced during passage through body tissue and losses due to prior reflections. Timing circuitry 170 generates timing signals which synchronize operation of the system; the timing signals being coupled to the circuitry 120 and 200 to alternately energize the transmitting and receiving modes, and also to reflector drive and display sweep circuitry 180, which generates the signals that control the oscillation of scanner 70 and the vertical and horizontal sweep signal for the display 21 and recorder 160.

In broad terms, operation of the system is as follows: Upon command from a trigger signal from the timing circuitry 170, the pulser 120 generates pulses which excite the segments of transducer 80. As is known in the art, the pulses can be relatively delayed so as to effect focusing of the ultrasound beam, and further focusing is provided by the lens 99. The ultrasound energy is reflected off the surface of scanner 70 and into the body 5, as represented in FIG. 2, the dashed line depicting the beam outline. When the ultrasound beam has been transmitted toward the body, the timing circuitry initiates the "receive" or "listen" mode by enabling the circuitry 200. Now, the transducer 80 serves to convert ultrasound energy, which is in the form of echoes reflected from the body and back off the scanner 70, into electrical signals. These signals are coupled, after processing by the circuitry 200, to the display 21. For a "B-scan" display, a sweep over a range of depths (which naturally results from the transmitted energy reflecting off different interfaces at successive depths in the body) corresponds to a horizontal scan line of the display. The second dimension of the desired cross-sectional image is obtained by a slower mechanical scan of scanner 70, the mechanical scanning range being illustrated by the double-headed arrow 73. Operation as described in this paragraph is generally in accordance with known techniques, novel aspects of the present invention residing, inter alia, in the dynamic focusing circuitry 200 to be described.

Figure 3:
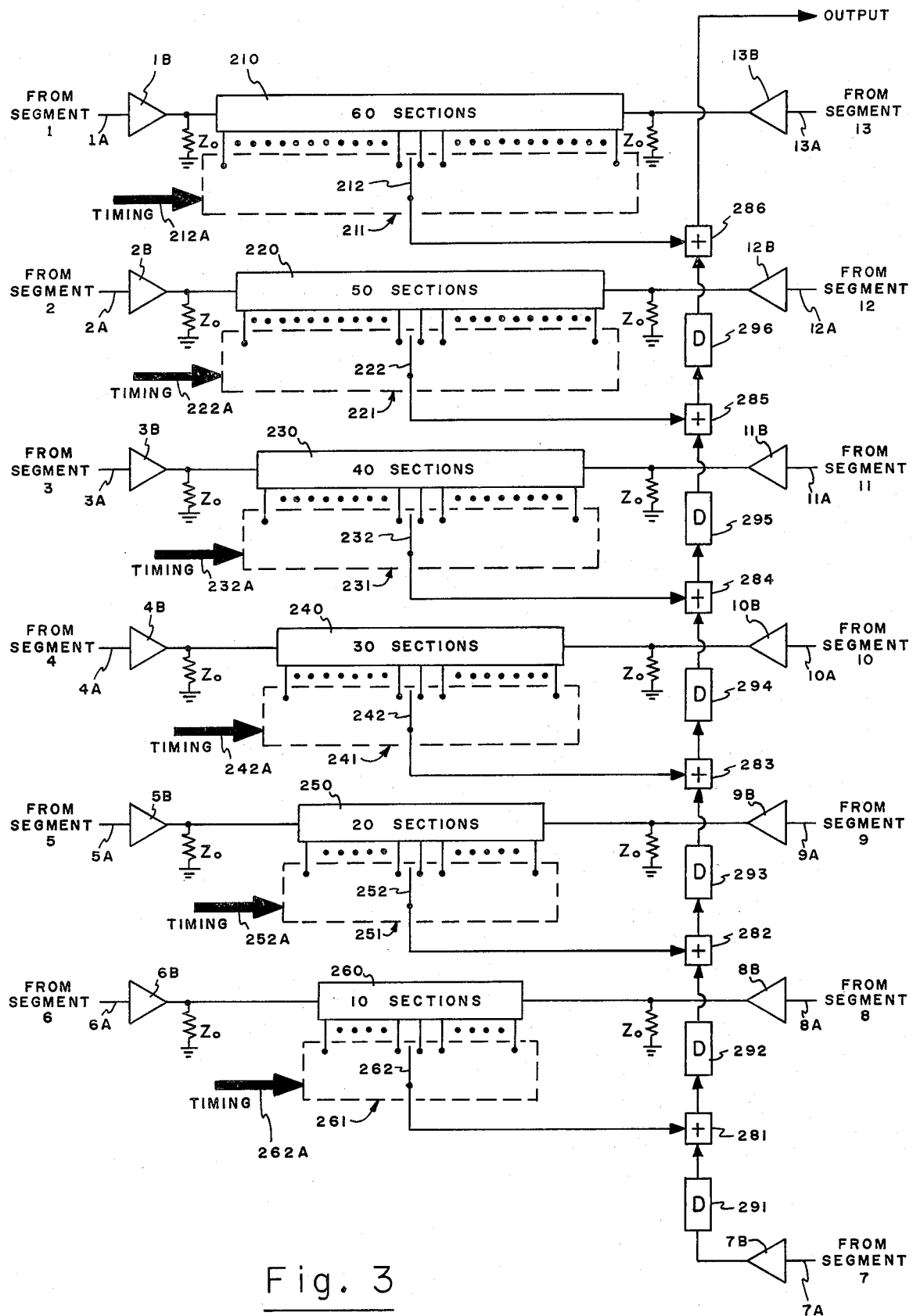
FIG. 3 is a block diagram of a dynamic focusing system in accordance with an embodiment of the invention.

Referring to FIG. 3, there is shown a block diagram of dynamic focusing system 200 in accordance with an embodiment of the invention. As noted above, in the present embodiment it is assumed for exemplary purposes that the segmented transducer 80 has thirteen elements or segments. The segments are, in this case, a central circular segment designated 1, and twelve concentric rings respectively designated 2 through 13 (FIG. 2) with lines 1A through 13A coupling the segments to the circuitry 200 and also to the pulser 120 as described above. It will be understood, however, that the invention is equally applicable to other types of transducers and other array formats. In the present embodiment six delay lines 210, 220, 230, 240, 250 and 260 are provided, each being terminated at both ends by a suitable impedance, $Z_o$. Each of the delay lines has a different number of stages with delay line 210 having the largest number of delay stages, delay line 220 having the next largest number of delay stages, and so on, with delay line 260 having the smallest number of stages. The outputs of transducer segments 1 through 13 are respectively connected, via preamplifiers 1B through 13B, to the delay lines. The signals from the first and last segments of the transducer (i.e., segments 1 and 13 in this case) are coupled to the opposite ends of the delay line having the largest number of stages (i.e., delay line 210 in this case). The adjacent pair of transducer segments (i.e., segments 2 and 12) are respectively connected, via preamplifiers 2B and 12B, to the opposite ends of the delay line having the next largest number of stages (i.e., delay line 220) and so on. Thus, in the embodiment of FIG. 3, the transducer segments 3 and 11 are connected, via preamplifiers 3B and 11B, to the opposing ends of delay line 230, the transducer segments 4 and 10 are connected, via preamplifiers 4B and 10B to the opposing ends of delay line 240, the transducer segments 5 and 9 are connected, via preamplifiers 5B and 9B to the opposing ends of delay line 250, and the transducer segments 6 and 8 are connected, via preamplifiers 6B and 8B to the opposing ends of delay line 260. In the present embodiment, the delay line 210 has sixty delay sections, the delay line 220 has fifty delay sections, the delay line 230 has forty delay sections, the delay line 240 has thirty delay sections, the delay line 250 has twenty delay sections, and the delay line 260 has ten delay sections. Each delay section of each delay line has an output tap coupled thereto, as illustrated by representative output taps at some of the stages in FIG. 3.

Each of the delay lines 210 through 260 has an associated "coupling means" or sampling circuit designated 211, 221, 231, 241, 251 and 261, respectively. Sampling circuits 211 through 261, which are described in further detail in conjunction with FIG. 4, each operates to sample the signal at different taps of its associated delay line. The instantaneous sampling positions of the sampling circuits are represented by the wipers 212, 222, 232, 242, 252 and 262. The wiper positions are determined by control signals designated 212A, 222A, 232A, 242A, 252A and 262A. As will be described further hereinbelow, these control signals are synchronized, such as by derivation from a common source.

The output of transducer segment 7 and the signals sampled by sampling circuits 211, 221, 231, 241, 251 and 261 are combined to obtain a signal that is ultimately displayed on display 21 (FIG. 1). The combining means used to effect the combination includes summing circuits 281, 282, 283, 284, 285 and 286, and fixed delay circuits 291, 292, 293, 294, 295 and 296. These summing and delay circuits are configured to introduce successively greater fixed delays to the signals from delay lines having successively lesser numbers of stages. In this manner, compensation is achieved for the different numbers of stages of the different delay lines. In particular, beginning with the output of transducer segment 7, and then continuing from segments 6,8 through segments 1,13, the signals are successively combined by summing circuits 281, 282 . . . 286, respectively, and a fixed delay is introduced to the running sum, before each new summation, by fixed delay circuits 291, 292 . . . 296, respectively. Stated another way, the output of transducer segment 7 is coupled, via delay circuit 291 to one input of summing circuit 281, the other input of summing circuit 281 receiving the signal from sampling circuit 261. The output of summing circuit 281 is then coupled, via fixed delay circuit 292, to one input of summing circuit 282, the other input of summing circuit 282 receiving the signal from sampling circuit 252, and so on.

The basic operation of the system can be understood as follows: Assume that each delay stage of each delay line has a characteristic delay of one delay unit, and that each of the fixed delay circuits 291, 292 . . . 296 has a characteristic delay of five delay units. As previously noted, an exemplary configuration of the present embodiment has delay lines 210, 220 . . . 260 as having sixty, fifty . . . ten stages, respectively, of delay. Assume now that each of the wipers 212, 222 . . . 262 is at the rightmost tap of its associated delay line. The rightmost column of Table I shows the number of units of delay experienced by the signals originating from each of the transducer segments (1-13) by virtue of the various delays in the FIG. 3 system.

TABLE I

| transducer segment # | left | center (units of delay) | right |
|---|---|---|---|
| 1 | 0 | 30 | 60 |
| 2 | 5 | 30 | 55 |
| 3 | 10 | 30 | 50 |
| 4 | 15 | 30 | 45 |
| 5 | 20 | 30 | 40 |
| 6 | 25 | 30 | 35 |
| 7 | 30 | 30 | 30 |
| 8 | 35 | 30 | 25 |
| 9 | 40 | 30 | 20 |
| 10 | 45 | 30 | 15 |
| 11 | 50 | 30 | 10 |
| 12 | 55 | 30 | 5 |
| 13 | 60 | 30 | 0 |

It is readily seen that the signal from transducer segment 13 experiences substantially no delay whereas the signal from transducer segment 1 experiences sixty units of delay since it traverses all sixty sections of delay line 210. It is also readily seen that the signal from transducer element or segment 13 will be subjected to zero delay. These results are indicated by the "0" opposite transducer segment 13 and the "60" opposite transducer segment 1 in the rightmost row of Table I. Also, it is seen that the signal from transducer segment 12 experiences five units of delay, while the signal from transducer segment 2 experiences fifty-five units of delay. This is readily established by noting that the fixed delay circuit 296 provides five units of delay, and (with the wiper 222 at its rightmost position), the delay line 220 contributes zero units of delay to the signal originating from transducer segment 12, and contributes fifty units of delay to the signal originating from transducer segment 2. The remaining entries in the rightmost column of Table I can be obtained in the same manner; i.e., by adding the appropriate number of delay units from the fixed delay circuits and the particular delay line in question. For example, the signal originating from transducer segment 7 will experience thirty units of delay (in all cases) since it travels through all six fixed delay circuits 291, 292 . . . 296.

The Table I also indicates the number of delay units experienced by the signals originating from each of the transducer segments when the wipers 212, 222 . . . 262 are in their leftmost position; these numbers being set forth in the leftmost column of Table I. It is seen that the listed delays are in the reverse order of those of the rightmost column of Table I. For example, the signal originating from transducer segment 1 will now experience zero delay units, while the signal originating from transducer segment 13 will now experience sixty units of delay. The remaining listed delays are, again, obtained in the same manner.

The central column of Table I indicates the number of units of delay experienced by the signal originating from each of the transducer segments when the wipers 212, 222 ... 262 are all at their central position (i.e., equally between the end taps) of their respective delay lines 210, 220 ... 260. In this case, it is seen that the signal originating from each transducer segment experiences a delay of thirty units. For example, the signals from transducer segments 1 and 13 each pass through half of the total sixty sections of delay line 210 (i.e., thirty units of delay for each). The signals originating from transducer segments 2 and 12 each experience twenty-five units of delay by passing through half of delay line 220, and each experience an additional five units of delay by virtue of the fixed delay circuit 296, thus totalling thirty units of delay for each of these two signals. A similar analysis reveals that thirty units of delay are experienced by the signals from each transducer segment for this case, as is consistent with the central row of Table I. Operation of the variable or dynamic focusing function can now be generally understood by invisioning what happens as the wipers 212, 222 ... 262 are swept in unison across the taps of their associated delay lines 210, 220 ... 260. When the wipers are at the center of each delay line, and the signals from all transducer segments experience the same delay (thirty units, in the present example), the system will be focused at the geometrical focus of the transducer. When the wipers are at the rightmost taps of their respective delay lines, the largest delays will be added to the signals from the lower numbered transducer segments (i.e., the more central segments in the present embodiment), and this results in the receiving system being focused at a "near" focal point which is closer to the transducer than the geometrical focal point. In particular, the increased delay added to the more central transducer segments compensate for the relatively shorter travel distance from the focal point to these transducer segments, and this results in the beam being effectively focused at a "near" focal point. The opposite result applies when the wipers are at the leftmost taps of their respective delay lines. In particular, this results in a "far" focus which is further from the transducer than its geometrical focus. For wiper positions intermediate those described, the focus will assume intermediate positions.

In operation, the pulser 120 (FIG. 2), upon command from the timing circuitry 170, energizes the segments of transducer 80 and the ultrasound beam is launched toward the body being investigated. (Typically, although not necessarily, the dynamic focusing is inactive during transmission and the beam is focused at the system's geometric focus. A predetermined time after pulsing, the time being a function of the distance to the desired near focus and the ultrasound velocity through the medium of travel, operation of the subsystem of FIG. 3 is initiated with the wipers 212, 222 ... 262 at their rightmost positions. The wipers are then swept simultaneously leftward, with the sweep time being set to substantially equal the expected travel time of the ultrasound in the body being investigated over the distance between the near and far foci. Accordingly, the focus determined by the system substantially tracks the beam position, so that echoes returning from any interface in the range of interest are automatically in focus. This general principle of dynamic focusing is well known, but the system and technique as set forth in FIG. 3, wherein delays are effectively "shared" in the manner described, is highly advantageous in reducing the number of components and in reducing the complexity generally required for the variable focusing operation.

Figure 4:
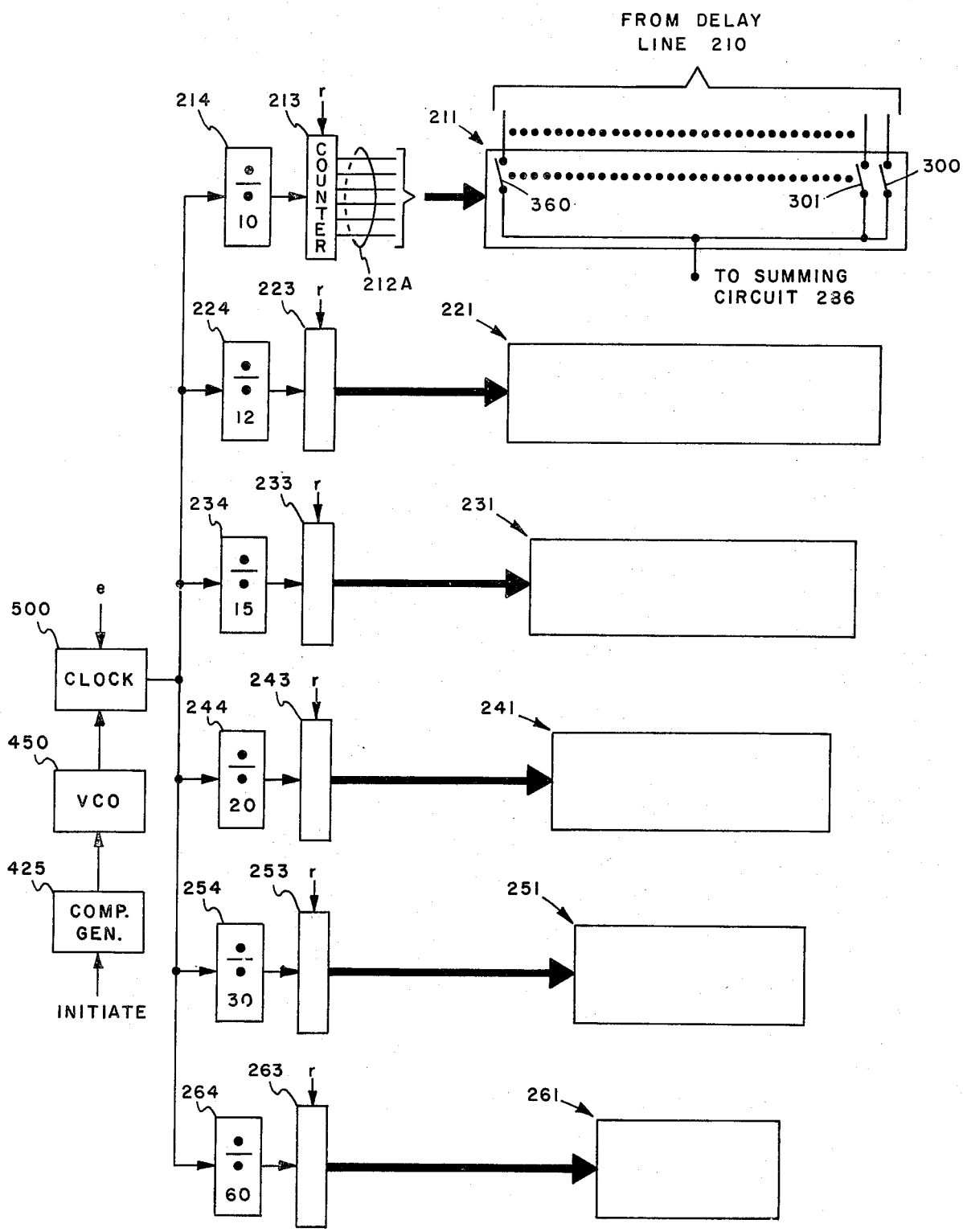
FIG. 4 is a block diagram which illustrates the sampling and clocking circuitry of the FIG. 3 embodiment.

Referring to FIG. 4, there is shown a block diagram of the clocking circuitry utilized to generate the control signals 212A, 222A ... 262A of FIG. 3, and there is also shown an embodiment of the coupling or sampling circuits 211, 221 ... 261, only one of the latter circuits being set forth in any detail, for ease of illustration. Each sampling circuit includes a plurality of address controlled switches, such as switches 300, 301 ... 360 of sampling circuit 211. Each of these switches has one terminal coupled to a tap of the associated delay line (FIG. 3). The other terminals of the switches are coupled together to form a common output of the sampling circuit (equivalent to the output as taken at the wiper 212 of FIG. 3). One switch at a time is closed for each sampling circuit, and the particular switch closed at any instant depends upon the address bits on lines 211A, 222A ... 262A, each switch having a unique address associated therewith. The addressable switches may be, for example, commercially available CMOS switches, such as the integrated circuit No. CD4051CMOS manufactured by RCA Corp., or any suitable addressable or programable switch packages made by other manufacturers. The addresses for each sampling circuit 211, 221 ... 261 are generated by respective counters 213, 223 ... 263 which count clock cycles from respective frequency dividers 214, 224 ... 264. These frequency dividers divide down the frequency from a clock 500. Thus, for example, at each successive cycle of the signal from frequency divider 214, the next higher count is generated by counter 213, and this constitutes the next higher address to the addressable switches of sampling circuit 211. The switches 300, 302 ... 360 are therefore sequentially activated from right-to-left, as are the switches of the other sampling circuits 221, 231 ... 261. In this manner, dynamic focusing is achieved as described above by sweeping successively from the near to the far focus of the imaging system.

Since each of the delay lines 210, 220 ... 260 of FIG. 3 has a different number of stages and taps, each of the sampling circuits 211, 221 ... 261 has an accordant different number of addressable switches; i.e. sixty-one for sampling circuit 211, fifty-one for sampling circuit 221, and so on. (It will be understood that the number of taps exceeds the number of stages by one, since there are taps at both ends of each delay line.) The addresses generated for each of the sampling circuits are generated at a different rate by the frequency dividers 214, 224 ... 264. In particular, the clock rate associated with each sampling circuit is obtained by dividing down a basic clock frequency from clock 500 using appropriately valued frequency dividers. This can be understood as follows: If the sweep period (i.e. the period during which all wipers of FIG. 3, or all switches of FIG. 4 sweep a full excursion from right-to-left) is designated as T, then the time period respectively associated with each stage of delay lines 210, 220 ... 260 will be T/60, T/50 ... T/10, respectively. Conversely, the ratio of clock frequencies associated with the delay lines 210, 220 ... 260 should be in the order 60:50:40:30:20:10, respectively. This means that frequencies of suitable ratios can be obtained by beginning with a basic clock frequency of 600F and dividing it down by 10, 12, 15, 20, 30, and 60, respectively, to obtain the desired resultant frequencies of 60F, 50F, 40F, 30F, 20F, and 10F. These divisions are obtained by the dividers 214, 224 . . . 264.

The sweep of foci from the near focal point to the far focal point is not linear, as can be readily shown from a geometrical analysis of the moving focal point. Accordingly, the frequencies at which the switches are swept in unison across their respective delay lines is obtained by using a varying master frequency. The varying master frequency is generated with a voltage controlled oscillator 450 under control of a ramp signal that is generated by ramp generator 425. Upon an initiating signal from the timing circuitry 170 (FIG. 2—and described above in connection with the operation of FIG. 3), which also provides an enable "e" to clock 500, the ramp generator 425 generates a downward sloping ramp signal which is coupled to the control terminal of voltage controlled oscillator 450. The oscillator voltage thus begins at an initial frequency of, say, 9.6 MHz and varies downward, as controlled by the ramp signal, toward a final frequency of, say, 2.4 MHz. Accordingly, the sweep, in unison, of the sampling circuits 211, 221 . . . 261 slows down as the focus moves outward. At the end of a scanline the counters 213, 223 . . . 263 are reset, as indicated by the signals "r" from the timing circuitry. With the counters reset to zero, the rightmost switches (e.g. 300 etc.) are set for the next cycle of counts (after enable e) which begins the next sweep of the switches across the delay lines.

The digital nature of the preferred implementation of the invention renders it advantageous to select the transducer ring configuration such that evenly spaced time delays can be employed therebetween for focusing. The necessary amounts of delay are a function of geometry, so the delays can be evenly spaced in time by appropriate selection of the transducer ring spacings.

The invention has been described with reference to a particular embodiment, but variations within the spirit and scope of the invention will occur to those skilled in the art. For example, it will be understood that while the illustrated embodiment is disclosed in terms of dynamic focusing over a range of distances from a transducer, it will be appreciated that the variable delay technique of the invention can be used for other purposes, for example, to steer a beam using an array of side-by-side, circular, or other arrays, of elements, where beam steering is achieved by varying the delay attributable to each element. Also, combinations of beam steering and dynamic focusing can be implemented. Further, it will be understood that the switches of FIG. 4 can be switched to and held at any desired coordinated position so that switchable focusing to any focus in the range can be obtained under operator control. This may be done, for example, by feeding in a desired number of clock pulses from clock 500.

I claim:

1. A variable delay system for receiving signals from a plurality of elements and for producing a sum of the signals from said elements, the contributions to said sum from different elements being delayed with respect to each other, and the relative delays attributable to signals from the different elements being variable as a function of time, comprising:

a plurality of delay lines;

means for respectively applying signals from pairs of said elements to opposite ends of different ones of said plurality of delay lines;

a plurality of coupling means respectively associated with said plurality of delay lines for sampling, as a predetermined function of time, the signals at different delay stages of their associated delay lines; and combining means for combining the outputs of said coupling means.

2. The system as defined by claim 1 wherein the signals at successive stages of said delay lines are sequentially sampled by said coupling means.

3. The system as defined by claim 1 further comprising means for generating a plurality of synchronized control signals and for applying said control signals to their respective coupling means to control the sampling positions of the coupling means.

4. The system as defined by claim 2 further comprising means for generating a plurality of synchronized control signals and for applying said control signals to their respective coupling means to control the sampling positions of the coupling means.

5. The system as defined by claim 1 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

6. The system as defined by claim 2 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

7. The system as defined by claim 3 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

8. The system as defined by claim 4 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

9. The system as defined by claim 5 wherein said combining means includes delay means which are operative to introduce successively greater fixed delays to the signals from delay lines having successively lesser numbers of stages.

10. The system as defined by claim 6 wherein said combining means includes delay means which are operative to introduce successively greater fixed delays to the signals from delay lines having successively lesser numbers of stages.

11. The system as defined by claim 7 wherein said combining means includes delay means which are operative to introduce successively greater fixed delays to the signals from delay lines having successively lesser numbers of stages.

12. The system as defined by claim 8 wherein said combining means includes delay means which are operative to introduce successively greater fixed delays to the signals from delay lines having successively lesser numbers of stages.

13. The system as defined by claim 3 wherein said means for generating a plurality of synchronized control signals comprises means for dividing a master clock frequency into a plurality of lower frequencies.

14. The system as defined by claim 4 wherein said means for generating a plurality of synchronized control signals comprises means for dividing a master clock frequency into a plurality of lower frequencies.

15. The system as defined by claim 8 wherein said means for generating a plurality of synchronized control signals comprises means for dividing a master clock frequency into a plurality of lower frequencies.

16. The system as defined by claim 12 wherein said means for generating a plurality of synchronized control signals comprises means for dividing a master clock frequency into a plurality of lower frequencies.

17. The system as defined by claim 3 wherein each of said coupling means comprises a plurality of switches coupled to the respective stages of its associated delay line, and wherein said control signals determine which switch of each coupling means is closed at a given time.

18. The system as defined by claim 7 wherein each of said coupling means comprises a plurality of switches coupled to the respective stages of its associated delay line, and wherein said control signals determine which switch of each coupling means is closed at a given time.

19. The system as defined by claim 11 wherein each of said coupling means comprises a plurality of switches coupled to the respective stages of its associated delay line, and wherein said control signals determine which switch of each coupling means is closed at a given time.

20. The system as defined by claim 16 wherein each of said coupling means comprises a plurality of switches coupled to the respective stages of its associated delay line, and wherein said control signals determine which switch of each coupling means is closed at a given time.

21. Apparatus for imaging a body, comprising:
    means for transmitting energy into the body;
    a transducer for converting echoes reflected from said body into electrical signals, said transducer being divided into a plurality of defined elements;
    a plurality of delay lines;
    means for respectively applying signals from pairs of said elements to opposite ends of different ones of said plurality of delay lines;
    a plurality of coupling means respectively associated with said plurality of delay lines for sampling, as a predetermined function of time, the signals at different delay stages of their associated delay lines; and
    combining means for combining the outputs of said coupling means to form an image representative signal.

22. Apparatus as defined by claim 21 wherein the signals at successive stages of said delay lines are sequentially sampled by said coupling means.

23. Apparatus as defined by claim 21 further comprising means for generating a plurality of synchronized control signals and for applying said control signals to their respective coupling means to control the sampling positions of the coupling means.

24. Apparatus as defined by claim 22 further comprising means for generating a plurality of synchronized control signals and for applying said control signals to their respective coupling means to control the sampling positions of the coupling means.

25. Apparatus as defined by claim 21 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

26. Apparatus as defined by claim 22 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

27. Apparatus as defined by claim 23 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

28. Apparatus as defined by claim 24 wherein said delay lines have respectively different numbers of stages, said elements are ordered transducer elements, and the signals from the first and last elements are respectively applied to opposite ends of the delay line having the largest number of stages, the signals from the second and next-to-last elements are respectively applied to the opposite ends of the delay line having the next-to-largest number of stages, and so on.

29. Apparatus as defined by claim 25 wherein said combining means includes delay means which are operative to introduce successively greater fixed delays to the signals from delay lines having successively lesser numbers of stages.

30. Apparatus as defined by claim 26 wherein said combining means includes delay means which are operative to introduce successively greater fixed delays to the signals from delay lines having successively lesser numbers of stages.

31. Apparatus as defined by claim 27 wherein said combining means includes delay means which are operative to introduce successively greater fixed delays to the signals from delay lines having successively lesser numbers of stages.

32. Apparatus as defined by claim 28 wherein said combining means includes delay means which are operative to introduce successively greater fixed delays to the signals from delay lines having successively lesser numbers of stages.

33. Apparatus as defined by claim 23 wherein said means for generating a plurality of synchronized control signals comprises means for dividing a master clock frequency into a plurality of lower frequencies.

34. Apparatus as defined by claim 32 wherein said means for generating a plurality of synchronized control signals comprises means for dividing a master clock frequency into a plurality of lower frequencies.

35. Apparatus as defined by claim 23 wherein each of said coupling means comprises a plurality of switches coupled to the respective stages of its associated delay line, and wherein said control signals determine which switch of each coupling means is closed at a given time.

36. Apparatus as defined by claim 25 wherein each of said coupling means comprises a plurality of switches coupled to the respective stages of its associated delay line, and wherein said control signals determine which switch of each coupling means is closed at a given time.

37. Apparatus as defined by claim 33 wherein each of said coupling means comprises a plurality of switches coupled to the respective stages of its associated delay line, and wherein said control signals determine which switch of each coupling means is closed at a given time.

38. A variable delay system for coupling a plurality of elements to a single element, comprising:
a plurality of delay lines having different numbers of stages;
means for respectively connecting pairs of said elements to opposite ends of different ones of said plurality of delay lines;
a plurality of coupling means respectively associated with said plurality of delay lines, each being operative to couple a selected delay stage of its associated delay line to said single element;
said coupling means being coupled to said single element via delay means which are operative to introduce successively greater delays between said single element and the delay lines having successively lesser numbers of stages; and
means for changing the selected delay stages to which said coupling means are coupled.

39. The system as defined by claim 38 wherein said means for changing the selected delay stages to which said coupling means are coupled are operative to sequence through successive delay stages of each delay line.

40. The system as defined by claim 39 wherein said means for changing the selected delay stages to which said coupling means are coupled are operative to sequence through successive delay stages in synchronism with each other.

41. A switchable delay system for receiving signals from a plurality of ordered transducer elements and for producing a combination of the signals from said elements, the contributions to said combination from different elements being delayed with respect to each other, and the relative delays attributable to signals from the different elements being switchable under operator control, comprising:
a plurality of delay lines having different numbers of steps;
means for respectively applying signals from pairs of said elements to opposite ends of different ones of said plurality of delay lines, the signals from the first and last elements being respectively applied to opposite ends of the delay line having the largest number of stages, the signals from the second and next-to-last elements being respectively applied to opposite ends of the delay line having the next-to-largest number of stages, and so on;
a combining circuit; and
a plurality of coupling means respectively associated with said plurality of delay lines, each operative to couple the signal at an operator selected one of said delay stages to said combining circuit.

42. The system as defined by claim 41 wherein each of said coupling means comprises a plurality of operator controllable switches coupled to the respective stages of its associated delay line.

43. Apparatus for imaging a body, comprising:
means for transmitting ultrasound energy into the body;
a transducer for converting ultrasound energy reflected from the body into electrical signals, said transducer being divided into a number of ordered segments;
a plurality of delay lines having respectively different numbers of stages;
means for respectively applying the signals from the first and last segments to opposing ends of the delay line having the largest number of stages, the signals from the second and next-to-last segments to opposing ends of the delay line having the next-to-largest number of stages, and so on;
a plurality of coupling means respectively associated with said plurality of delay lines for sampling, as a function of time, the signals at different delay stages of their respective delay lines; and
means for combining the outputs of said coupling means to form an image-representative signal.

44. Apparatus as defined by claim 43 wherein the signals at successive stages of said delay lines are sequentially sampled by said coupling means.

45. Apparatus as defined by claim 43 further comprising means for generating a plurality of synchronized control signals and for applying said control signals to their respective coupling means to control the sampling positions of the coupling means.

46. Apparatus as defined by claim 44 further comprising means for generating a plurality of synchronized control signals and for applying said control signals to their respective coupling means to control the sampling positions of the coupling means.

47. Apparatus as defined by claim 43 wherein said combining means includes delay means which are operative to introduce successively greater fixed delays to the signals from delay lines having successively lesser numbers of stages.

48. Apparatus as defined by claim 44 wherein said combining means includes delay means which are operative to introduce successively greater fixed delays to the signals from delay lines having successively lesser numbers of stages.

49. Apparatus as defined by claim 45 wherein said combining means includes delay means which are operative to introduce successively greater fixed delays to the signals from delay lines having successively lesser numbers of stages.

50. Apparatus as defined by claim 46 wherein said combining means includes delay means which are operative to introduce successively greater fixed delays to the signals from delay lines having successively lesser numbers of stages.

51. Apparatus as defined by claim 45 wherein said means for generating a plurality of synchronized control signals comprises means for dividing a master clock frequency into a plurality of lower frequencies.

52. Apparatus as defined by claim 49 wherein said means for generating a plurality of synchronized control signals comprises means for dividing a master clock frequency into a plurality of lower frequencies.

53. Apparatus as defined by claim 45 wherein each of said coupling means comprises a plurality of switches coupled to the respective stages of its associated delay line, and wherein said control signals determine which switch of each coupling means is closed at a given time.

54. Apparatus as defined by claim 51 wherein each of said coupling means comprises a plurality of switches coupled to the respective stages of its associated delay line, and wherein said control signals determine which switch of each coupling means is closed at a given time.

55. Apparatus as defined by claim 52 wherein each of said coupling means comprises a plurality of switches coupled to the respective stages of its associated delay line, and wherein said control signals determine which switch of each coupling means is closed at a given time.

56. Apparatus as defined by claim 43, wherein the segments of said transducer have geometries selected such that evenly spaced time delays can be employed in conjunction with said segments to effect a given focus of said transducer.

57. Apparatus as defined by claim 46, wherein the segments of said transducer have geometries selected such that evenly spaced time delays can be employed in conjunction with said segments to effect a given focus of said transducer.

58. Apparatus as defined by claim 50, wherein the segments of said transducer have geometries selected such that evenly spaced time delays can be employed in conjunction with said segments to effect a given focus of said transducer.

* * * * *